United States Patent
Choi et al.

(10) Patent No.: US 11,711,975 B2
(45) Date of Patent: Jul. 25, 2023

(54) NEAR-INFRARED ABSORBERS, NEAR-INFRARED ABSORBING/BLOCKING FILMS, PHOTOELECTRIC DEVICES, ORGANIC SENSORS, AND ELECTRONIC DEVICES

(71) Applicant: Samsung Electronics Co., Ltd., Suwon-si (KR)

(72) Inventors: Hyesung Choi, Seoul (KR); Hwang Suk Kim, Suwon-si (KR); Ohkyu Kwon, Seoul (KR); Takkyun Ro, Hwaseong-si (KR); Kwang Hee Lee, Hwaseong-si (KR); Dong-Seok Leem, Seongnam-si (KR); Bum Woo Park, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 332 days.

(21) Appl. No.: 17/022,222

(22) Filed: Sep. 16, 2020

(65) Prior Publication Data
US 2021/0083199 A1    Mar. 18, 2021

(30) Foreign Application Priority Data
Sep. 16, 2019   (KR) .......................... 10-2019-0113716

(51) Int. Cl.
*H01L 51/50* (2006.01)
*H10K 85/60* (2023.01)
(Continued)

(52) U.S. Cl.
CPC ......... *H10K 85/657* (2023.02); *C07D 513/04* (2013.01); *C07F 7/0816* (2013.01);
(Continued)

(58) Field of Classification Search
None
See application file for complete search history.

(56) References Cited

FOREIGN PATENT DOCUMENTS

| CN | 103936653 A | 7/2014 |
|---|---|---|
| JP | 20170025039 A | 2/2017 |

(Continued)

OTHER PUBLICATIONS

Extended European Search Report dated Mar. 3, 2021 for corresponding European Application No. 20196400.4.
(Continued)

*Primary Examiner* — Gregory D Clark
(74) *Attorney, Agent, or Firm* — Harness, Dickey & Pierce, P.L.C.

(57) ABSTRACT

A near-infrared absorber includes a compound represented by Chemical Formula 1. A near-infrared absorbing/blocking film, a photoelectric device, an organic sensor, and an electronic device may include the near-infrared absorber.

[Chemical Formula 1]

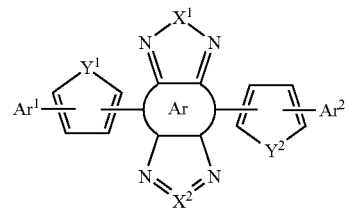

In Chemical Formula 1, $X^1$, $X^2$, $Y^1$, $Y^2$, Ar, $Ar^1$, and $Ar^2$ are the same as defined in the detailed description.

15 Claims, 7 Drawing Sheets

(51) Int. Cl.
 *C07D 513/04* (2006.01)
 *C07F 7/08* (2006.01)
 *H10K 85/40* (2023.01)
 *H10K 85/20* (2023.01)
 *H10K 30/00* (2023.01)

(52) U.S. Cl.
 CPC ......... *H10K 85/211* (2023.02); *H10K 85/215* (2023.02); *H10K 85/40* (2023.02); *H10K 85/649* (2023.02); *H10K 85/655* (2023.02); *H10K 85/6572* (2023.02); *H10K 30/00* (2023.02)

(56) References Cited

FOREIGN PATENT DOCUMENTS

| JP | 2018-111673 | * | 7/2018 | ............. H01L 51/50 |
| JP | 2018-111673 A | | 7/2018 | |
| JP | 2018-111675 A | | 7/2018 | |
| WO | WO-2018/015320 A1 | | 1/2018 | |

OTHER PUBLICATIONS

Zhang et al. "Near-Infrared Fluorescent Thienothiadiazole Dyes with Large Stokes Shifts and high Photostability", 1. J. Org. Chem. 2017, 82, 5597-5606.

Qian et al. "Simple and Efficient Near-Infrared Organic Chromophores for Light-Emitting Diodes with Single Electroluminescent Emission Above 1000nm", 1. Adv. Mater. 2009, 21, 111-116.

* cited by examiner

NEAR-INFRARED ABSORBERS, NEAR-INFRARED ABSORBING/BLOCKING FILMS, PHOTOELECTRIC DEVICES, ORGANIC SENSORS, AND ELECTRONIC DEVICES

CROSS-REFERENCE TO RELATED APPLICATION

This application claims priority to and the benefit of, under 35 U.S.C. § 119, Korean Patent Application No. 10-2019-0113716 filed in the Korean Intellectual Property Office on Sep. 16, 2019, the entire contents of which are incorporated herein by reference.

BACKGROUND

1. Field

A near-infrared (NIR) absorber, a near-infrared absorbing/blocking film, a photoelectric device, an organic sensor, and an electronic device are disclosed.

2. Description of the Related Art

An imaging device is used in a digital camera and a camcorder, etc., to capture an image and to store it as an electrical signal, and the imaging device includes a sensor separating incident light according to a wavelength and converting each component to an electrical signal.

Recently, photoelectric devices in a near-infrared region have been researched to improve sensitivity of a sensor in low illumination environment or to be used as a biometric device.

SUMMARY

Some example embodiments provide a near-infrared absorber having improved near-infrared light absorption characteristics.

Some example embodiments provide a film including the near-infrared absorber.

Some example embodiments provide a photoelectric device including the near-infrared absorber.

Some example embodiments provide an organic sensor including the near-infrared absorber or the photoelectric device.

Some example embodiments provide an electronic device including the photoelectric device or the organic sensor.

According to some example embodiments, a near-infrared absorber including a compound represented by Chemical Formula 1 is provided.

[Chemical Formula 1]

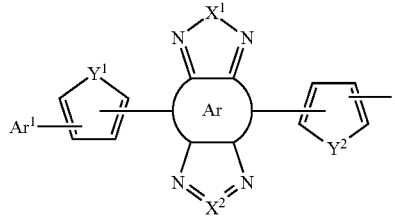

In Chemical Formula 1,

Ar may be a substituted or unsubstituted C6 to C30 aromatic ring, a substituted or unsubstituted C3 to C30 heteroaromatic ring, or a combination thereof, $X^1$ may be O, S, Se, Te, S(=O), S(=$O_2$), $NR^a$, C(=O), $CR^bR^c$, or $SiR^dR^e$, wherein $R^a$, $R^b$, $R^c$, $R^d$, and $R^e$ are independently hydrogen, a C1 to C6 alkyl group, a C1 to C6 haloalkyl group, a halogen, or a cyano group, $X^2$ may be O, S, Se, Te, C, S(=O), or S(=$O_2$), $Y^1$ and $Y^2$ may independently be O, S, Se, Te, S(=O), S(=$O_2$), $NR^a$, $SiR^bR^c$, or $C(R^dR^e)$, wherein $R^a$, $R^b$, $R^c$, $R^d$, and $R^e$ may independently be hydrogen, deuterium, a C1 to C6 alkyl group, a C1 to C6 haloalkyl group, a halogen, or a cyano group, and $Ar^1$ and $Ar^2$ are independently a functional group represented by Chemical Formula A.

[Chemical Formula A]

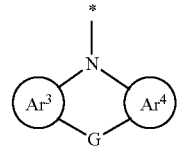

In Chemical Formula A, $Ar^3$ and $Ar^4$ may independently be a substituted or unsubstituted C6 to C30 arene group, or a substituted or unsubstituted C3 to C30 heteroarene group, G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2, and

* may be a linking point.

In Chemical Formula 1, Ar may be an unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, Ar may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

Chemical Formula A may be represented by one of Chemical Formula A-1 to Chemical Formula A-5.

[Chemical Formula A-1]

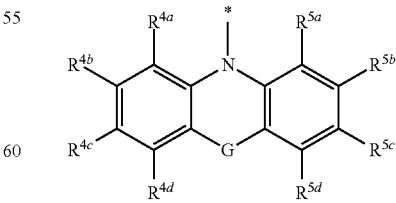

In Chemical Formula A-1,

G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2, and $R^{4a}$ to $R^{4d}$ and $R^{5a}$ to $R^{5d}$ have structures such that $R^{4a}$ to $R^{4d}$ and $R^{5a}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4a}$ to $R^{4d}$ may be linked to each other to provide a 5-membered aromatic ring or a 6-membered aromatic ring, and/or two adjacent groups of $R^{5a}$ to $R^{5d}$ may be linked to each other to provide a 5-membered aromatic ring or a 6-membered aromatic ring.

[Chemical Formula A-2]

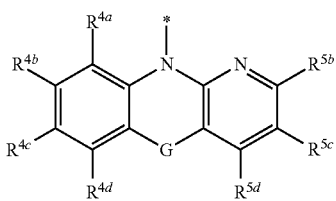

In Chemical Formula A-2,

G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2, and $R^{4a}$ to $R^{4d}$ and $R^{5b}$ to $R^{5d}$ may have structures such that $R^{4a}$ to $R^{4d}$ and $R^{5b}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4a}$ to $R^{4d}$ may be linked to each other to provide a 5-membered aromatic ring or a 6-membered aromatic ring, and/or two adjacent groups of $R^{5b}$ to $R^{5d}$ may be linked to each other to provide a 5-membered aromatic ring or a 6-membered aromatic ring.

[Chemical Formula A-3]

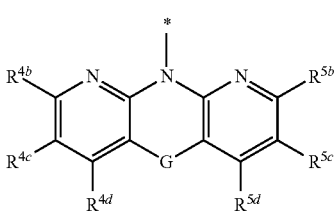

In Chemical Formula A-3,

G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group and a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2, and $R^{4b}$ to $R^{4d}$ and $R^{5b}$ to $R^{5d}$ may have structures such that $R^{4b}$ to $R^{4d}$ and $R^{5b}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4b}$ to $R^{4d}$ may be linked to each other to provide a 5-membered aromatic ring or a 6-membered aromatic ring, and/or two adjacent groups of $R^{5b}$ to $R^{5d}$ may be linked to each other to provide a 5-membered aromatic ring or a 6-membered aromatic ring.

[Chemical Formula A-4]

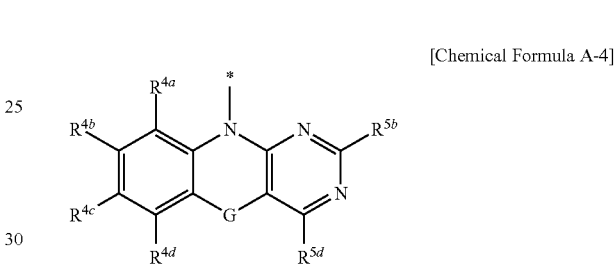

In Chemical Formula A-4,

G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2, and $R^{4a}$ to $R^{4d}$ and $R^{5b}$ and $R^{5d}$ may have structures such that $R^{4a}$ to $R^{4d}$ and $R^{5b}$ and $R^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4a}$ to $R^{4d}$ may be linked to each other to provide a 5-membered aromatic ring or a 6-membered aromatic ring.

[Chemical Formula A-5]

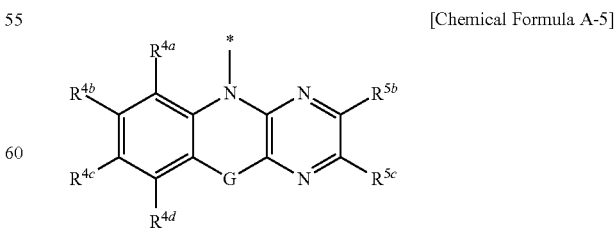

In Chemical Formula A-5,

G may be a single bond, —O—, —S—, —Se—, —Te—, —N=, —$NR^a$—, —$SiR^bR^c$—, —$GeR^dR^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may be independently present or linked to each other to form a ring, and n of —(CR$^f$R$^g$)$_n$— is an integer of 1 or 2, and R$^{4a}$ to R$^{4d}$ and R$^{5b}$ and R$^{5c}$ may have structures such that R$^{4a}$ to R$^{4d}$ and R$^{5b}$ to R$^{5b}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of R$^{4a}$ to Rod may be linked to each other to provide a 5-membered aromatic ring or a 6-membered aromatic ring, and/or two adjacent groups of R$^{5b}$ and R$^{5c}$ may be linked to each other to provide a 5-membered aromatic ring or a 6-membered aromatic ring.

The near-infrared absorber may have a peak absorption wavelength in a wavelength region of about 700 nm to about 3000 nm.

According to some example embodiments, a near-infrared absorbing/blocking film including the near-infrared absorber is provided.

According to some example embodiments, a photoelectric device includes a first electrode and a second electrode facing each other, and an active layer disposed between the first electrode and the second electrode, wherein the active layer includes the aforementioned near-infrared absorber including the compound represented by Chemical Formula 1.

According to some example embodiments, an organic sensor including the photoelectric device is provided.

According to some example embodiments, an electronic device including the photoelectric device or the organic sensor is provided.

The near-infrared absorber may exhibit light absorption characteristics in a near-infrared region, and thus may be effectively used in photoelectric devices and/or organic sensors.

DETAILED DESCRIPTION

Figure 1:
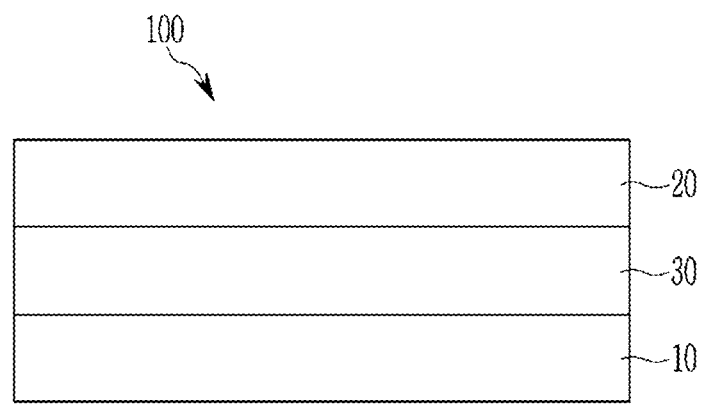
FIG. 1 is a cross-sectional view showing a photoelectric device according to some example embodiments.

Hereinafter, some example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath the other element.

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B and C).

As used herein, when specific definition is not otherwise provided, "substituted" refers to replacement of a hydrogen of a compound or a functional group by a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, or a combination thereof.

As used herein, when specific definition is not otherwise provided, "hetero" refers to one including 1 to 4 heteroatoms selected from N, O, S, Se, Te, Si, and P.

As used herein, when a definition is not otherwise provided, "aromatic ring" refers to a functional group in which all atoms in the cyclic functional group have a p-orbital, and wherein these p-orbitals are conjugated and "heteroaromatic ring" refers to the aromatic ring including a heteroatom. The "aromatic ring" means a C6 to C30 arene group, for example a C6 to C20 arene group or a C6 to C30 aryl group, for example a C6 to C20 aryl group. In addition, the "heteroaromatic ring" may be a C3 to C30 heteroarene group, for example, a C3 to C20 heteroarene group, or a C3 to C30 heteroaryl group, for example, a C3 to C20 heteroaryl group.

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, P, and Si.

As used herein, when a definition is not otherwise provided, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heteroaryl group" refers to an aryl group including at least one heteroatom selected from N, O, S, Se, Te, P, and Si instead of carbon (C) in the ring. When the heteroaryl group is a fused ring, at least one of rings of the heteroaryl group may have a heteroatom or each ring may have a heteroatom.

As used herein, when a definition is not otherwise provided, "ring" refers to an aromatic ring, a non-aromatic ring, a heteroaromatic ring, a hetero non-aromatic ring, a fused ring thereof, and/or a combination thereof.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as $=CR^{x'}-(CR^{x}R^{y})_p-CR^{y'}(CN)_2$ wherein $R^x$, $R^y$, $R^{x'}$, and $R^{y'}$ are each independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

Hereinafter, a near-infrared absorber according to some example embodiments is described. The near-infrared absorber may be referred to herein interchangeably as a "near-infrared absorbing compound."

The near-infrared absorber includes a compound represented by Chemical Formula 1.

[Chemical Formula 1]

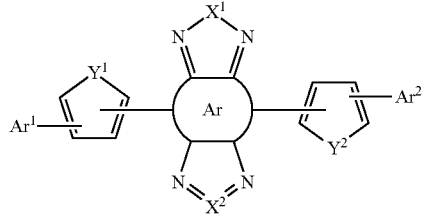

In Chemical Formula 1,

Ar may be a substituted or unsubstituted C6 to C30 aromatic ring, a substituted or unsubstituted C3 to C30 heteroaromatic ring, or a combination thereof, $X^1$ may be O, S, Se, Te, S(=O), S(=O$_2$), NR$^a$, C(=O), CR$^b$R$^c$, or SiR$^d$R$^e$ (wherein R$^a$, R$^b$, R$^c$, R$^d$, and R$^e$ may independently be hydrogen, deuterium, C1 to C6 alkyl group, a C1 to C6 haloalkyl group, a halogen, or a cyano group), $X^2$ may be O, S, Se, Te, C, S(=O), or S(=O$_2$), $Y^1$ and $Y^2$ may independently be O, S, Se, Te, S(=O), S(=O)$_2$, NR$^a$, SiR$^b$R$^c$, or CR$^d$R$^e$ (wherein R$^a$, R$^b$, R$^c$, R$^d$, and R$^e$ may independently be hydrogen, deuterium, a C1 to C6 alkyl group, a C1 to C6 haloalkyl group, a halogen, or a cyano group), and Ar$^1$ and Ar$^2$ may independently be a functional group represented by Chemical Formula A.

[Chemical Formula A]

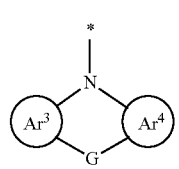

In Chemical Formula A,

Ar$^3$ and Ar$^4$ may independently be a substituted or unsubstituted C6 to C30 arene group, for example a substituted or unsubstituted C6 to C20 arene group, or a substituted or unsubstituted C3 to C30 heteroarene group, for example a substituted or unsubstituted C3 to C20 heteroarene group, G may be a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein R$^a$, R$^b$, R$^c$, R$^d$, R$^e$, R$^f$, R$^g$, R$^h$, and R$^i$ may independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may be independently present or linked to each other to form a ring, and n of —(CR$^f$R$^g$)$_n$— is an integer of 1 or 2), and

* may be a linking point.

The near-infrared absorber has a donor-acceptor-donor structure in which a substituted or unsubstituted cyclic amine group having an electron donating property (Chemical Formula A) is linked to the $Y^1$-containing ring and the $Y^2$-containing ring to a core of a conjugated structure having electron accepting properties and thereby, may have an improved light absorption characteristics to effectively absorb light in a near-infrared wavelength region and may exhibit good electrical properties.

The near-infrared absorber may have a peak absorption wavelength (λmax) of, for example, greater than or equal to about 700 nm, for example greater than or equal to about 750 nm, greater than or equal to about 780 nm, greater than or equal to about 790 nm, greater than or equal to about 800 nm, greater than or equal to about 810 nm, greater than or equal to about 820 nm, or greater than or equal to about 830 nm. The near-infrared absorber may have a peak absorption wavelength (λmax) of, for example, about 700 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm.

In Chemical Formula 1, $X^1$ and $X^2$ may be the same as or different from each other.

In Chemical Formula 1, $X^1$ and $X^2$ may independently be O or S.

In Chemical Formula 1, $Y^1$ and $Y^2$ may be the same as or different from each other.

In Chemical Formula 1, $Y^1$ and $Y^2$ may independently be O, S, or $C(CN)_2$.

In Chemical Formula 1, Ar may be an unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, Ar may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

The $Y^1$-containing ring and $Y^2$-containing ring may be linked at a symmetrical position with respect to Ar or at an asymmetrical position with respect to Ar.

In Chemical Formula 1, Ar may be one moiety of a set of moieties represented by Chemical Formula B-1, each moiety including at least one aromatic ring and left and right linking groups.

[Chemical Formula B-1]

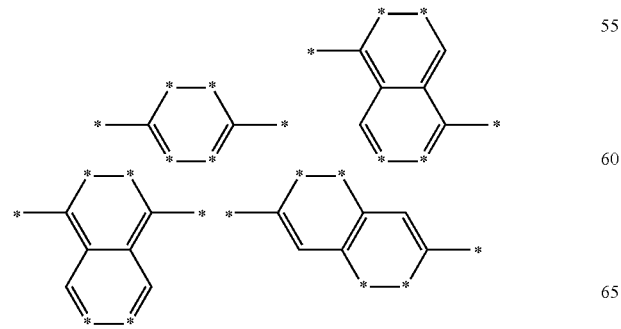

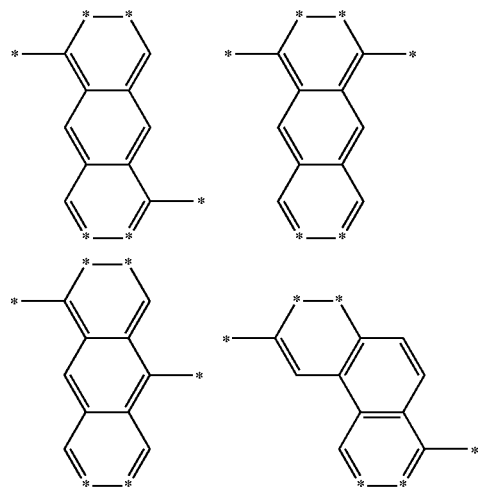

In Chemical Formula B-1, hydrogen of each aromatic ring may be replaced by a halogen, a cyano group, a C1 to C10 alkyl group, or a C1 to C10 haloalkyl group, separate adjacent pairs of *'s in the at least one aromatic ring are portions which are fused with separate, respective ones of an N—$X^1$—N-containing pentagonal ring of Chemical Formula 1 and an N=$X^2$=N-containing pentagonal ring of Chemical Formula 1, and *'s of the left and right linking groups are linking portions of the $Y^1$-containing ring and $Y^2$-containing ring of Chemical Formula 1.

In Chemical Formula 1, Ar may be one moiety of a set of moieties represented by Chemical Formula B-2, each moiety including at least one aromatic ring and left and right linking groups.

[Chemical Formula B-2]

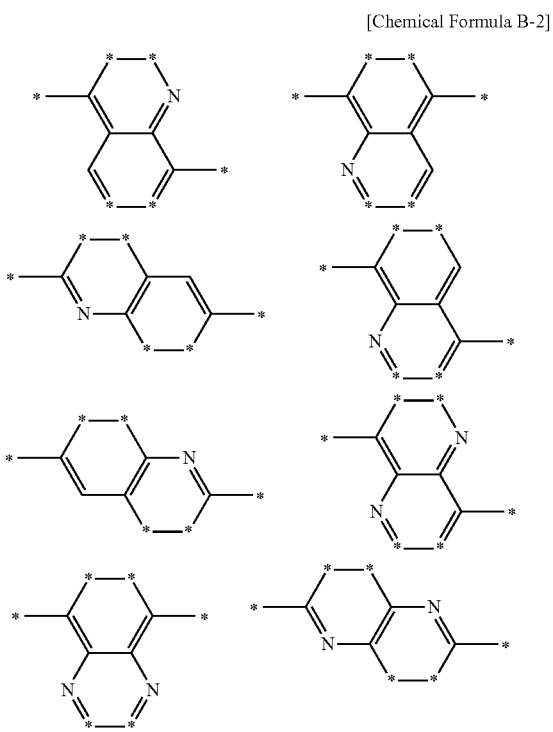

-continued

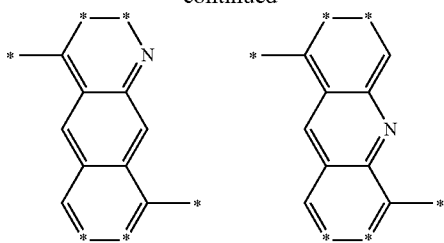

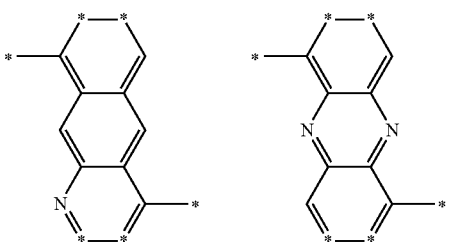

In Chemical Formula B-2, hydrogen of each aromatic ring may be replaced by a halogen, a cyano group, a C1 to C10 alkyl group, or a C1 to C10 haloalkyl group, separate adjacent pairs of *'s in the at least one aromatic ring are portions which are fused with separate, respective ones of an N—$X^1$—N-containing pentagonal ring of Chemical Formula 1 and an N=$X^2$=N-containing pentagonal ring of Chemical Formula 1, and *'s of the left and right linking groups are linking portions of the $Y^1$-containing ring and $Y^2$-containing ring of Chemical Formula 1.

In Chemical Formula 1, the $Y^1$-containing ring and $Y^2$-containing ring may be represented by Chemical Formula C.

[Chemical Formula C]

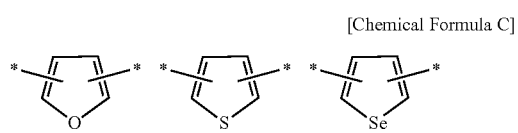

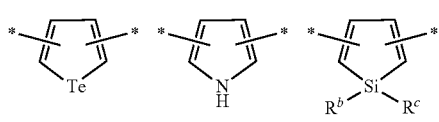

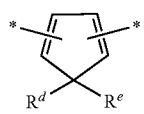

In Chemical Formula C,
$R^a$ to $R^e$ may independently be hydrogen, deuterium, a C1 to C6 alkyl group, a halogen, a cyano group, or a combination thereof.

The Chemical Formula A may be represented by one of Chemical Formula A-1 to Chemical Formula A-5.

[Chemical Formula A-1]

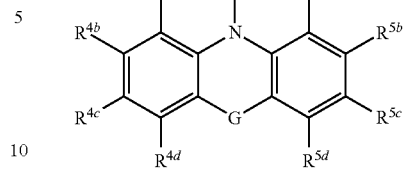

In Chemical Formula A-1,
G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$— (wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2), and $R^{4a}$ to $R^{4d}$ and $R^{5a}$ to $R^{5d}$ may have structures such that a) $R^{4a}$ to $R^{4d}$ and $R^{5a}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or b) optionally two adjacent groups of $R^{4a}$ to $R^{4d}$ may be linked to each other to provide a 5-membered aromatic ring or a 6-membered aromatic ring and optionally two adjacent groups of $R^{5a}$ to $R^{5d}$ may be linked to each other to provide a 5-membered aromatic ring or a 6-membered aromatic ring.

[Chemical Formula A-2]

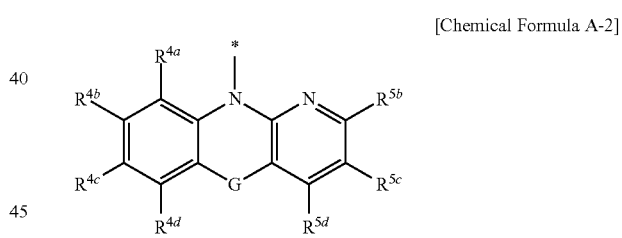

In Chemical Formula A-2,
G may be a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$— (wherein $R^a$, $R^b$, $R^c$, $R^d$, $R^e$, $R^f$, $R^g$, $R^h$, and $R^i$ may independently be hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ may be independently present or linked to each other to form a ring, and n of —$(CR^fR^g)_n$— is an integer of 1 or 2), and $R^{4a}$ to $R^{4d}$ and $R^{5b}$ to $R^{5d}$ have structures such that a) $R^{4a}$ to $R^{4d}$ and $R^{5b}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or b) optionally two adjacent groups of $R^{4a}$ to $R^{4d}$ may be linked to each other to provide a 5-membered aromatic ring or a 6-membered aromatic ring and optionally two adjacent groups of $R^{5b}$ to $R^{5d}$ may be linked to each other to provide a 5-membered aromatic ring or a 6-membered aromatic ring.

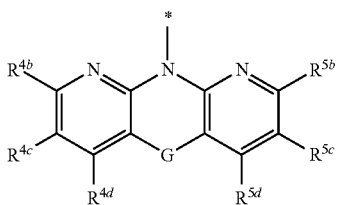

[Chemical Formula A-3]

In Chemical Formula A-3,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))— (wherein R$^a$, R$^b$, R$^c$, R$^d$, R$^e$, R$^f$, R$^g$, R$^h$, and R$^i$ may independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^b$ and R$^i$ may be independently present or linked to each other to form a ring, and n of —(CR$^f$R$^g$)$_n$— is an integer of 1 or 2), and $R^{4b}$ to $R^{4d}$ and $R^{5b}$ to $R^{5d}$ may have structures such that a) $R^{4b}$ to $R^{4d}$ and $R^{5b}$ to $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or b) optionally two adjacent groups of $R^{4b}$ to $R^{4d}$ may be linked to each other to provide a 5-membered aromatic ring or a 6-membered aromatic ring and optionally two adjacent groups of $R^{5b}$ to $R^{5d}$ may be linked to each other to provide a 5-membered aromatic ring or a 6-membered aromatic ring.

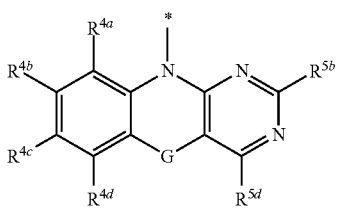

[Chemical Formula A-4]

In Chemical Formula A-4,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))— (wherein R$^a$, R$^b$, R$^c$, R$^d$, R$^e$, R$^f$, R$^g$, R$^h$, and R$^i$ may independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^b$ and R$^i$ may be independently present or linked to each other to form a ring, and n of —(CR$^f$R$^g$)$_n$— is an integer of 1 or 2), and $R^{4a}$ to $R^{4d}$ and $R^{5b}$ and $R^{5d}$ may have structures such that a) $R^{4a}$ to $R^{4d}$ and $R^{5b}$ and $R^{5d}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or b) optionally two adjacent groups of $R^{4a}$ to $R^{4d}$ may be linked to each other to provide a 5-membered aromatic ring or a 6-membered aromatic ring.

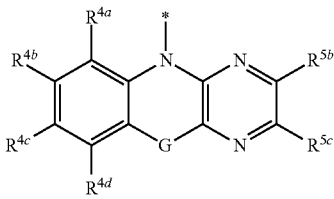

[Chemical Formula A-5]

In Chemical Formula A-5,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))— (wherein R$^a$, R$^b$, R$^c$, R$^d$, R$^e$, R$^f$, R$^g$, R$^h$, and R$^i$ may independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may be independently present or linked to each other to form a ring, and n of —(CR$^f$R$^g$)$_n$— is an integer of 1 or 2), and $R^{4a}$ to $R^{4d}$ and $R^{5b}$ and $R^{5c}$ may have structures such that a) $R^{4a}$ to $R^{4d}$ and $R^{5b}$ to $R^{5c}$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or b) optionally two adjacent groups of $R^{4a}$ to $R^{4d}$ may be linked to each other to provide a 5-membered aromatic ring or a 6-membered aromatic ring and optionally two adjacent groups of $R^{5b}$ and $R^{5c}$ may be linked to each other to provide a 5-membered aromatic ring or a 6-membered aromatic ring.

The near-infrared absorber may exhibit good charge transfer characteristics, and thus, it has good photoelectric conversion characteristics that absorb light and convert it into an electrical signal, and thus may be effectively used as a photoelectric conversion material for photoelectric devices.

The near-infrared absorber has good heat resistance, and thus may prevent or reduce thermal decomposition during deposition, and thus may be repeatedly deposited. The near-infrared absorber may be thermally or vacuum deposited and may be deposited, for example, by sublimation. For example, deposition by sublimation may be confirmed by thermogravimetric analysis (TGA), and at a thermogravimetric analysis at a pressure of less than or equal to about 10 Pa, a temperature at which a 10% weight loss relative to an initial weight may be less than or equal to about 450° C. and a temperature at which a 50% weight loss relative to an initial weight may be less than or equal to about 500° C. For example, at a thermogravimetric analysis of the near-infrared absorber at a pressure of less than or equal to about 10 Pa, for example temperature at which a 10% weight loss relative to an initial weight may be about 230° C. to about 450° C. and a temperature at which a 50% weight loss relative to an initial weight may be about 300° C. to about 500° C.

Some example embodiments provide a near-infrared absorbing/blocking film including the near-infrared absorber.

The near-infrared absorbing/blocking film may be applied to various fields requiring light absorption characteristics in a near-infrared wavelength region.

The near-infrared absorber has both light absorption characteristics and photoelectric characteristics in a near-infrared wavelength region, it may be effectively used as a photoelectric conversion material.

FIG. 1 is a cross-sectional view of a photoelectric device according to some example embodiments.

Referring to FIG. 1, a photoelectric device 100 according to some example embodiments includes a first electrode 10 and a second electrode 20 facing each other and an active layer 30 between the first electrode 10 and the second electrode 20.

A substrate (not shown) may be disposed at the side of the first electrode 10 or the second electrode 20. The substrate may be for example made of (e.g., may at least partially comprise) an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 or the second electrode 20 is an anode and the other is a cathode. For example, the first electrode 10 may be a cathode and the second electrode 20 may be an anode.

At least one of the first electrode 10 or the second electrode 20 may be a light-transmitting electrode and the light-transmitting electrode may be for example made of a conductive oxide such as an indium tin oxide (ITO), indium zinc oxide (IZO), zinc oxide (ZnO), tin oxide ($SnO_2$), aluminum tin oxide (AlTO), and fluorine doped tin oxide (FTO), or a metal thin layer of a single layer or a multilayer. When one of the first electrode 10 or the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The active layer is a layer including a p-type semiconductor and an n-type semiconductor to provide a pn junction, which is a layer producing excitons by receiving light from outside and then separating holes and electrons from the produced excitons.

The p-type semiconductor and the n-type semiconductor may be independently a light absorber that is configured to absorb (e.g., selectively absorb) light in at least a portion of a wavelength region and the aforementioned near-infrared absorber may be a p-type semiconductor or an n-type semiconductor. For example, the aforementioned near-infrared absorber may be used for a p-type semiconductor and fullerene or a fullerene derivative may be included as an n-type semiconductor. Accordingly, it will be understood that the active layer 30 may at least partially comprise the aforementioned near-infrared absorber (e.g., may include the near-infrared absorber and either fullerene or a fullerene derivative). The active layer 30, and thus the photoelectric device 100 may have improved near-infrared light absorption characteristics (e.g., may have improved sensitivity to light in a near-infrared wavelength region, improved absorbance of light in the near-infrared wavelength region, etc.) and thus improved photoelectric conversion performance and/or efficiency based on the active layer including the aforementioned near-infrared absorber. In some example embodiments, the active layer 30 may be a near-infrared absorbing/blocking film that includes the near-infrared absorber.

The active layer 30 may include an intrinsic layer in which the aforementioned near-infrared absorber (p-type semiconductor) and fullerene or a fullerene derivative (n-type semiconductor) are co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer 30 may further include a p-type layer and/or an n-type layer in addition to the intrinsic layer. The p-type layer may include the aforementioned near-infrared absorber and the n-type layer may include the aforementioned n-type semiconductor. For example, they may be included in various combinations of p-type layer/I layer, I layer/n-type layer, p-type layer/I layer/n-type layer, and the like.

The photoelectric device 100 may further include an auxiliary layer between the first electrode 10 and the active layer 30 and/or the second electrode 20 and the active layer 30. This photoelectric device (e.g., optoelectronic device) is shown in FIG. 2.

Figure 2:
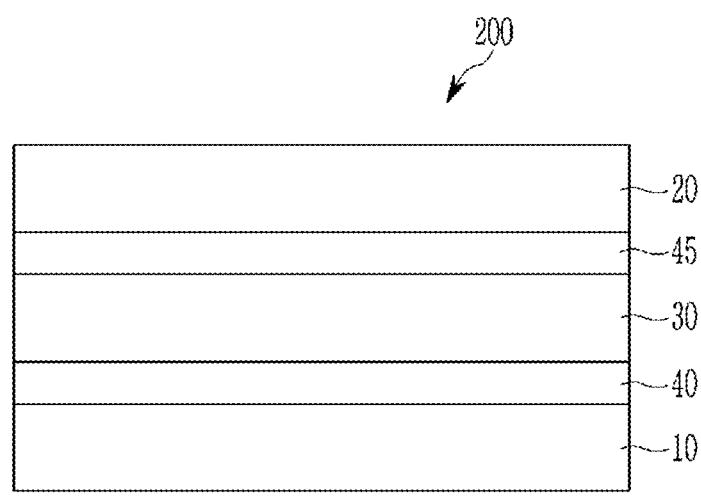
FIG. 2 is a cross-sectional view showing a photoelectric device according to some example embodiments.

FIG. 2 is a cross-sectional view showing a photoelectric device according to some example embodiments.

Referring to FIG. 2, a photoelectric device 200 includes a first electrode 10 and a second electrode 20 facing each other, an active layer 30 between the first electrode 10 and the second electrode 20, a first auxiliary layer 40 between the first electrode 10 and the active layer 30, and a second auxiliary layer 45 between the second electrode 20 and the active layer 30. In some example embodiments, only one of the first auxiliary layer 40 or the second auxiliary layer 45 is included in the photoelectric device 200. The first auxiliary layer 40 and the second auxiliary layer 45 may each be a charge auxiliary layer that may make holes and electrons separated in the active layer 30 be transported more easily to improve efficiency of the photoelectric device 200.

The charge auxiliary layers 40 and/or 45 may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layers 40 and/or 45 may include for example the aforementioned near-infrared absorber.

The photoelectric devices 100 and 200 may further include an anti-reflection layer (not shown) on one surface of the first electrode 10 or the second electrode 20. The anti-reflection layer is disposed at a light incidence side and lowers reflectance of light of incident light and thereby light absorbance is further improved. For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5 and may include for example at least one of a metal oxide, a semi-metal oxide, a metal sulfide, or an organic material having a refractive index within the ranges. The anti-reflection layer may include, for example a metal oxide or semi-metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the photoelectric devices 100 and 200, when light enters said photoelectric device 100 and/or 200 and thus enters the active layer 30 thereof from (e.g., via) the first electrode 10 or the second electrode 20, and the active layer 30 thus absorbs the light in a particular (or, alternatively, predetermined)) wavelength region, excitons may be generated thereinside. The excitons are separated into holes and electrons in the active layer 30, and the separated holes are transported to an anode that is one of the first electrode 10 or the second electrode 20 and the separated electrons are transported to the cathode that is the other of the first electrode 10 and the second electrode 20 so as to flow (e.g., induce, generate, etc.) a current.

The photoelectric devices 100 and 200 may be applied to a solar cell, an image sensor, a photodetector, a photosensor, and an organic light emitting diode (OLED), but is not limited thereto.

The photoelectric devices 100 and 200 may be applied to (e.g., included in) an organic sensor. The organic sensor may be an organic CMOS sensor, for example, an organic CMOS infrared light sensor or an organic CMOS image sensor.

In some example embodiments, the photoelectric device 100 may include the near-infrared absorber in any of the elements thereof, including, in addition to or alternative to the active layer 30, one or more of the first electrode 10 or the second electrode 20. In some example embodiments, the photoelectric device 200 may include the near-infrared absorber in any of the elements thereof, including, in addition to or alternative to the active layer 30 and/or one or more of the charge auxiliary layers 40/45, one or more of the first electrode 10 or the second electrode 20.

Figure 3:
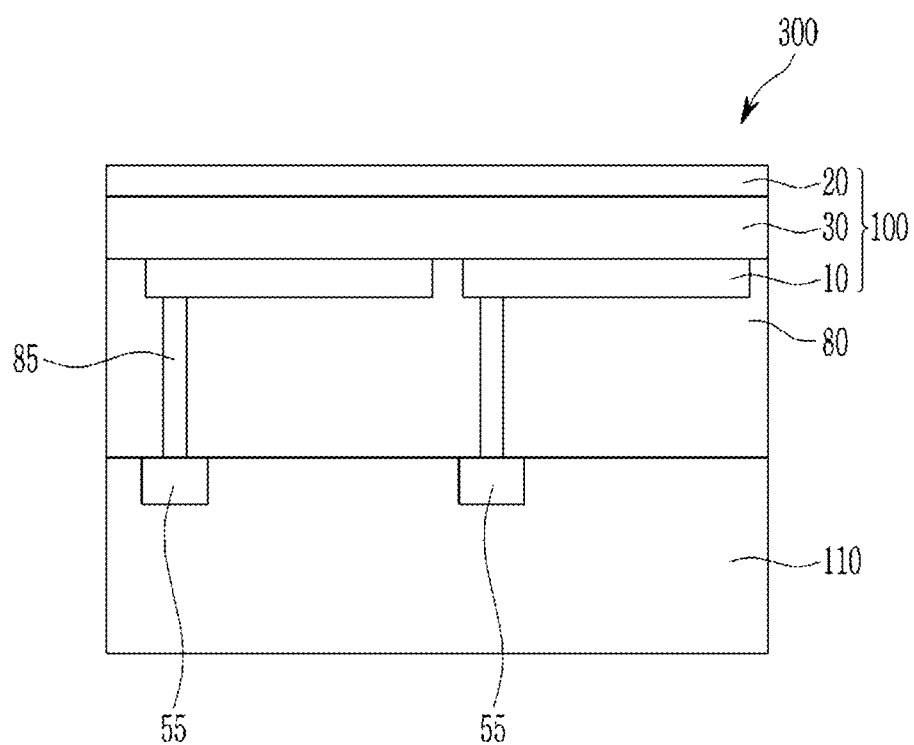
FIG. 3 is a cross-sectional view showing an organic sensor according to some example embodiments.

FIG. 3 is a cross-sectional view showing an organic sensor according to some example embodiments.

The organic sensor 300 according to some example embodiments includes a semiconductor substrate 110, an insulation layer 80, and a photoelectric device 100.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric device 100 and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal wire and pad. The insulation layer 80 may be made of an inorganic insulating material such as a silicon oxide and/or a silicon nitride, or a low dielectric constant (low K) material such as SiC, SiCOH, SiCO, and SiOF. The insulation layer 80 has a trench 85 exposing the charge storage 55. The trench 85 may be filled with fillers.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the first electrode 10 may be arranged in this order. In addition, the photoelectric device according to FIG. 1 is illustrated in the drawing, but the photoelectric device according to FIG. 2 may also be applied in the same manner.

The first electrode 10 and the second electrode 20 may both be transparent electrodes, and the active layer 30 may be the same as described above with reference to FIGS. 1 and 2. The active layer 30 may selectively absorb light in a near-infrared wavelength region. Incident light from the side of the second electrode 20 may be photoelectrically converted by mainly absorbing light in a near-infrared wavelength region in the active layer 30. As noted above with reference to FIG. 1, the active layer 30 may include the aforementioned near-infrared absorber and thus may have improved sensitivity to near-infrared light, such that the operational performance and/or efficiency of the organic sensor 300 in absorbing and/or converting incident near-infrared light into electrical signals (e.g., photoelectric conversion performance and/or efficiency) may be improved.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

The organic sensor according to some example embodiments may be an organic infrared light sensor, for example an iris sensor or a depth sensor.

The iris sensor identifies a person by using unique iris characteristics of every person and specifically, taking an image of an eye of a user within an appropriate distance, processing the image, and comparing it with his/her stored image.

The depth sensor identifies a shape and a location of an object from its three-dimensional information by taking an image of the object within an appropriate distance with a user and processing the image. This depth sensor may be for example used as a face recognition sensor.

Figure 4:
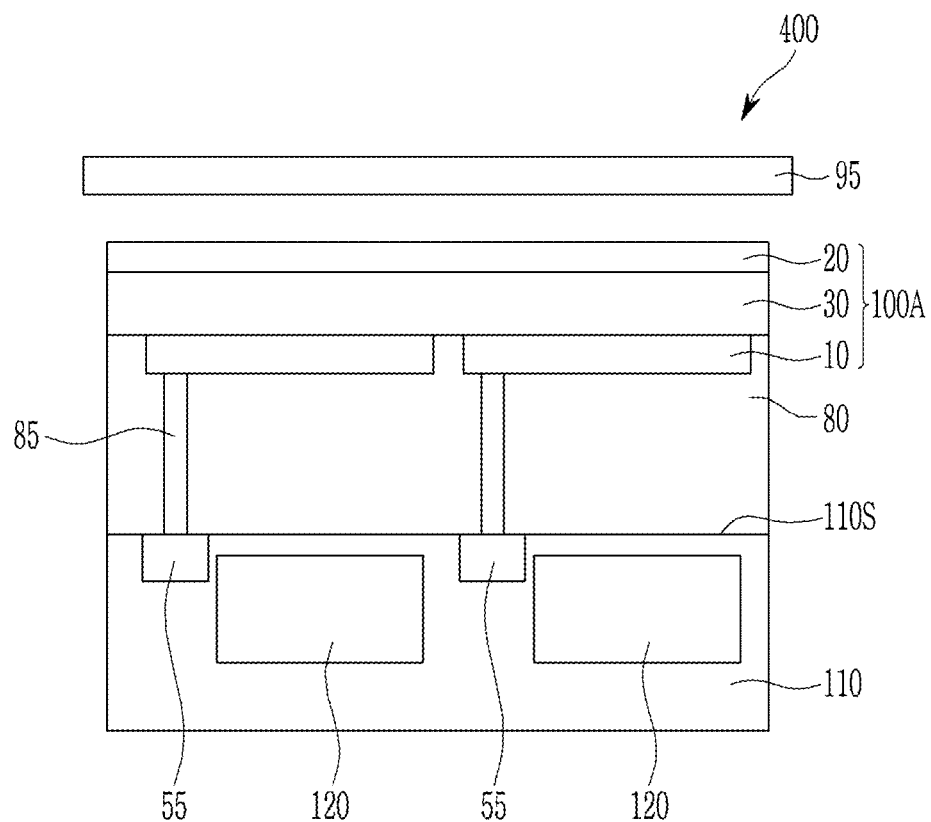
FIG. 4 is a cross-sectional view showing an organic sensor according to some example embodiments.

FIG. 4 is a cross-sectional view showing an organic sensor according to some example embodiments.

The organic sensor according to some example embodiments may include a plurality of sensors having different functions. For example, at least one of the plurality of sensors having different functions may be a biometric sensor, and the biometric sensor may be for example an iris sensor, a depth sensor, a fingerprint sensor, a blood vessel distribution sensor, and the like, but is not limited thereto. For example, one sensor of the plurality of sensors having different functions may be an iris sensor and another sensor of the plurality of sensors having different functions may be a depth sensor.

For example, a plurality of sensors may include, for example a first infrared light sensor configured to sense (e.g., selectively absorb and/or convert (into electrical signals, e.g., photoelectrically convert)) light in an infrared region (e.g., infrared wavelength region) having a first wavelength ($\lambda_1$) in an infrared wavelength region and a second infrared light sensor configured to sense (e.g., selectively absorb and/or convert (into electrical signals, e.g., photoelectrically convert)) light in an infrared region having a second wavelength ($\lambda_2$) in an infrared wavelength region (e.g., a same or different infrared wavelength region as the infrared wavelength region including the first wavelength ($\lambda_1$)).

The first wavelength ($\lambda_1$) and the second wavelength ($\lambda_2$) may be for example different in a wavelength region of about 750 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

For example, one of the first wavelength ($\lambda_1$) or the second wavelength ($\lambda_2$) may belong to a wavelength region of about 780 nm to about 900 nm and the other of the first wavelength ($\lambda_1$) or the second wavelength ($\lambda_2$) may belong to a wavelength region of about 830 nm to about 1000 nm.

For example, one of the first wavelength ($\lambda_1$) or the second wavelength ($\lambda_2$) may belong to a wavelength region of about 780 nm to about 840 nm and the other of the first wavelength ($\lambda_1$) or the second wavelength ($\lambda_2$) may belong to a wavelength region of about 910 nm to about 970 nm.

For example, one of the first wavelength ($\lambda_1$) or the second wavelength ($\lambda_2$) may belong to a wavelength region of about 800 nm to about 830 nm and the other of the first wavelength ($\lambda_1$) or the second wavelength ($\lambda_2$) may belong to a wavelength region of about 930 nm to about 950 nm.

For example, one of the first wavelength ($\lambda_1$) or the second wavelength ($\lambda_2$) may belong to a wavelength region of about 805 nm to about 815 nm and the other of the first wavelength ($\lambda_1$) or the second wavelength ($\lambda_2$) may belong to a wavelength region of about 935 nm to about 945 nm.

For example, one of the first wavelength ($\lambda_1$) or the second wavelength ($\lambda_2$) may about 810 nm and the other of the first wavelength ($\lambda_1$) or the second wavelength ($\lambda_2$) may be about 940 nm.

The organic sensor 400 according to some example embodiments includes a dual bandpass filter 95, a first infrared light sensor 100A, an insulation layer 80, and a semiconductor substrate 110 integrated with a second infrared light sensor 120, such that the second infrared light sensor 120 is at least partially embedded within the semiconductor substrate 110. As shown in FIG. 4, the first infrared light sensor 100A and the second infrared light sensor 120 may be stacked, e.g., may overlap in a vertical direction that is perpendicular to the top surface 110S of the semiconductor substrate 110.

As shown in FIG. 4, dual bandpass filter 95 may be disposed on a front side of the organic sensor 400 and may selectively transmit infrared light (e.g., light in an infrared wavelength region) including the first wavelength ($\lambda_1$) and infrared light including the second wavelength ($\lambda_2$) and may block and/or absorb other light. Herein, other light may include light in an ultraviolet (UV) and visible region.

As shown in FIG. 4, the first infrared light sensor 100A may be the same as the photoelectric device 100 according to some example embodiments, including the example embodiments described with reference to FIG. 1, but it will be understood that, in some example embodiments, the first infrared light sensor 100A may be the same as the photoelectric device 200 according to some example embodiments, including the example embodiments described with reference to FIG. 2.

As shown in FIG. 4, the second infrared light sensor 120 may be integrated in the semiconductor substrate 110 and may be a photo-sensing device. The semiconductor substrate 110 (e.g., encompassed within a volume space defined by outer surfaces of the semiconductor substrate 110) may be for example a silicon substrate and may be integrated with the second infrared light sensor 120, the charge storage 55, and a transmission transistor (not shown).

The second infrared light sensor 120 may be a photodiode (e.g., a silicon-based photodiode) and may sense (e.g., absorb) entered light, and sensed information is transferred by the transmission transistor. Herein, the light entered into the second infrared light sensor 120 is light that passes through (e.g., is selectively transmitted by) the dual bandpass filter 95 and the first infrared light sensor 100A and may be infrared light in a particular (or, alternatively, predetermined) region including the second wavelength ($\lambda_2$). All infrared light in a particular (or, alternatively, predetermined) region including the first wavelength ($\lambda_1$) may be absorbed by the active layer 30 and may not reach the second infrared light sensor 120. In this case, a separate filter for wavelength selectivity with respect to the light entered into the second infrared light sensor 120 is not separately needed. However, for the time when all infrared light in a particular (or, alternatively, predetermined) region including the first wavelength ($\lambda_1$) is not absorbed by active layer 30, a filter between the first infrared light sensor 100A and the second infrared light sensor 120 may be further disposed.

Accordingly, in the organic sensor 400, the first infrared light sensor 100A may be understood to include a photoelectric device (e.g., photoelectric device 100 and/or 200) configured to sense (e.g., selectively absorb and/or convert (into electrical signals, e.g., photoelectrically convert)) light in a first near-infrared wavelength region of incident light (e.g., a first near-infrared wavelength region including the first wavelength ($\lambda_1$)), and the second infrared light sensor 120 may be understood to include an additional sensor configured to selectively absorb and/or convert (into electrical signals, e.g., photoelectrically convert) light in a separate wavelength region of incident light (e.g., a second near-infrared wavelength region that is different from the first near-infrared wavelength region and includes the second wavelength ($\lambda_2$) and excludes the first wavelength ($\lambda_1$)).

The organic sensor according to some example embodiments may include two infrared light sensors respectively performing separately functions and thus may work as a combination sensor. In addition, two sensors performing separately functions are stacked in each pixel, and thus the number of pixel performing functioning of each sensor is twice increased while maintaining a size and resultantly, sensitivity may be much improved.

As noted above with reference to FIG. 1, the active layer 30, or any portion of the photoelectric device 100 and/or 200, may include the aforementioned near-infrared absorber and thus may have improved sensitivity to and/or absorbance of near-infrared light, such that the operational performance and/or efficiency of the organic sensor 400 in absorbing and/or photoelectrically converting incident near-infrared light into electrical signals (e.g., photoelectric conversion performance and/or efficiency) may be improved. In some example embodiments, the second infrared light sensor 120 may include the aforementioned near-infrared absorber and thus may have improved sensitivity to and/or absorbance of near-infrared light, such that the operational performance and/or efficiency of the organic sensor 400 in absorbing and/or converting incident near-infrared light into electrical signals (e.g., photoelectric conversion performance and/or efficiency) may be improved.

Figure 5:
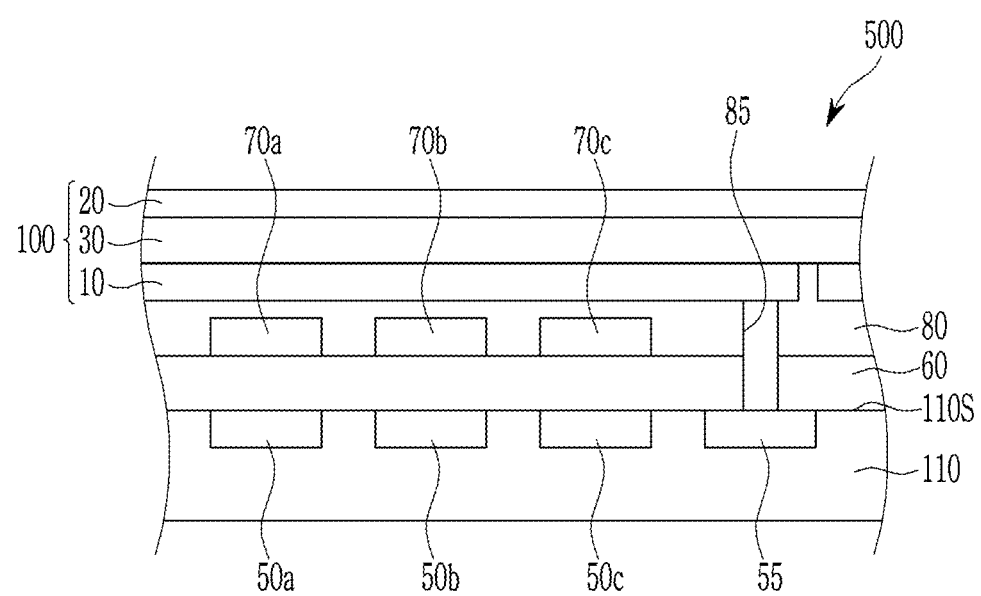
FIG. 5 is a cross-sectional view showing an organic sensor according to some example embodiments.

FIG. 5 is a cross-sectional view showing an example of an organic sensor according to some example embodiments.

An organic sensor according to some example embodiments may be an organic CMOS image sensor.

Referring to FIG. 5, an organic sensor 500 according to some example embodiments includes a semiconductor substrate 110 integrated with photo-sensing devices (e.g., photodiodes, including silicon-based photodiodes) 50*a*, 50*b*, and 50*c*, a transmission transistor (not shown), and a charge storage 55, a lower insulation layer 60, color filter 70*a*, 70*b*, and 70*c*, an insulation layer 80, and a photoelectric device 100.

The semiconductor substrate 110 may be integrated with photo-sensing devices 50*a*, 50*b*, and 50*c* such that the photo-sensing devices 50*a*, 50*b*, and 50*c* are at least partially embedded within the semiconductor substrate 110 and are vertically overlapped by the photoelectric device 100 in the vertical direction that is perpendicular to the top surface 110S, a transmission transistor (not shown), and a charge storage 55. The photo-sensing devices 50*a*, 50*b*, and 50*c* may be photodiodes (e.g., silicon-based photodiodes) that may be configured to sense (e.g., selectively absorb and/or convert (into electrical signals, e.g., photoelectrically convert)) light in different visible wavelength regions.

The photo-sensing devices 50*a*, 50*b*, and 50*c*, the transmission transistor, and/or the charge storage 55 may be integrated in each pixel. For example, the photo-sensing device 50*a* may be included in a red pixel, the photo-sensing device 50*b* may be included in a green pixel, and the photo-sensing device 50*c* may be included in a blue pixel.

The photo-sensing devices 50*a*, 50*b*, and 50*c* sense (e.g., selectively absorb and/or convert (into electrical signals, e.g., photoelectrically convert)) incident light, the information sensed by the photo-sensing devices may be transferred by the transmission transistor, the charge storage 55 is electrically connected to the photoelectric device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50*a* and 50*b*.

The lower insulation layer 60 is formed on the metal wire and the pad. The lower insulation layer 60 may include a same or different material composition as the insulation layer 80.

Color filters 70*a*, 70*b*, and 70*c* are formed on the lower insulation layer 60. The color filters 70*a*, 70*b*, and 70*c* includes a red filter 70*a* formed in a red pixel, a green filter 70*b* formed in a green pixel, and a blue filter 70*c* formed in a blue pixel.

The insulation layer 80 (also referred to as upper insulation layer) is formed on the color filters 70*a*, 70*b*, and 70*c*. The insulation layer 80 eliminates steps caused by the color filters 70*a*, 70*b*, and 70*c* and planarizes the surface.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the first electrode 10 may be arranged in this order. In addition, the photoelectric device according to FIG. 1 is illustrated in the drawing, but the photoelectric device according to FIG. 2 may also be applied in the same manner.

The first electrode 10 and the second electrode 20 may both be transparent electrodes, and the active layer 30 is the same as described above. The active layer 30 may selectively absorb and/or convert (into electrical signals, e.g., photoelectrically convert) light in a near-infrared wavelength region. As noted above with regard to photoelectric devices 100 and 200, any portion of the photoelectric device 100 (e.g., first electrode 10, second electrode 20, and/or active layer 30) may include the aforementioned near-infrared absorber.

Incident light from the side of the second electrode 20 may be photoelectrically converted by mainly absorbing light in a near infra-red wavelength region in the active layer 30. Light in the remaining wavelength region may pass through the first electrode 10 and the color filters 70*a*, 70*b*, and 70*c*, the light in a red wavelength region passing through the color filter 70*a* may be sensed by the photo-sensing device 50*a*, the light in a green wavelength region passing through the color filter 70*b* may be sensed by the photo-sensing device 50*b*, and the light in a blue wavelength region passing through the color filter 70*c* may be sensed by the photo-sensing device 50*c*.

As noted above with reference to FIG. 1, the active layer 30 may include the aforementioned near-infrared absorber and thus may have improved sensitivity to near-infrared light, such that the operational performance and/or efficiency of the organic sensor 500 in absorbing and/or converting incident near-infrared light into electrical signals (e.g., photoelectric conversion performance and/or efficiency) may be improved.

Accordingly, where an organic sensor includes a photoelectric device that includes the near-infrared absorber and is configured to selectively absorb and/or convert (into electrical signals, e.g., photoelectrically convert) light in a first near-infrared wavelength region, the organic sensor may include an additional sensor that includes a plurality of photodiodes (e.g., photo-sensing devices 50*a*, 50*b*, 50*c*) at least partially embedded within the semiconductor substrate and configured to selectively absorb and/or convert (into electrical signals, e.g., photoelectrically convert) light in separate visible wavelength regions (e.g., red, blue, and/or green light).

The organic sensor may be applied to (e.g., included in) various electronic devices, for example and the electronic devices may include for example a camera, a camcorder, a mobile phone internally having them, a display device, a security device, or a medical device, but are not limited thereto.

Figure 6:
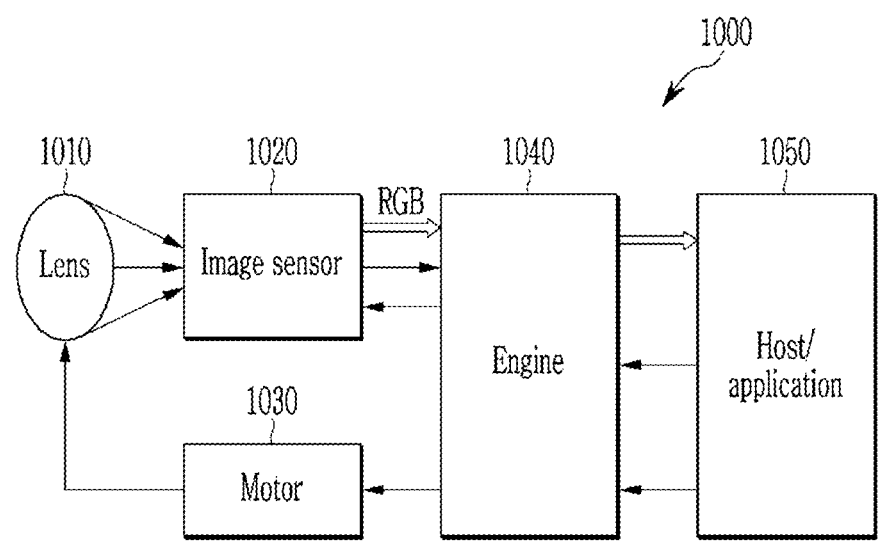
FIG. 6 is a block diagram of a digital camera including an organic sensor according to some example embodiments.

FIG. 6 is a block diagram of a digital camera including an image sensor according to some example embodiments.

Referring to FIG. 6, a digital camera 1000 includes a lens 1010, an image sensor 1020, a motor 1030, and an engine 1040. The image sensor 1020 may be one of image sensors according to some example embodiments, including the example embodiments shown in FIGS. 3 to 5. The lens 1010 concentrates incident light on the image sensor 1020. The image sensor 1020 generates RGB data for received light through the lens 1010. In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050. In example embodiments, the motor 1030, engine 1040, and host/application 1050 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. One or more of the processor (not shown), memory (not shown), motor 1030, engine 1040, or host/application 1050 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the processor (not shown), memory (not shown), motor 1030, engine 1040, or host/application 1050, or the like according to any of the example embodiments as described herein.

Hereinafter, some example embodiments are illustrated in more detail with reference to examples. However, the example embodiments are not limited to these examples.

SYNTHESIS EXAMPLES

Synthesis Example 1: Synthesis of Compound Represented by Chemical Formula 1-1

[Chemical Formula 1-1]

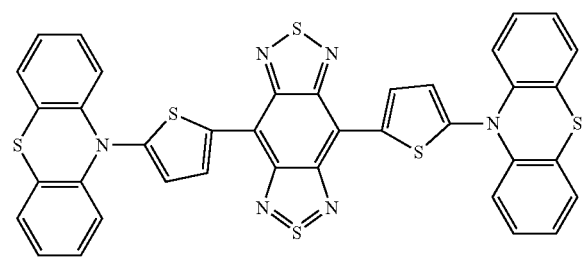

10-(5-(tributylstannyl)thiophen-2-yl)-10H-phenothiazine (0.58 g, 1.02 mmol), 4,8-dibromobenzo[1,2-c;4,5-c]bis([1,2,5]thiadiazole) (0.3 g, 0.85 mmol), and (tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.28 g (Yield: 45%) of a product.

MALDI-TOF molecular weight analysis: m/z 752

Synthesis Example 2: Synthesis of Compound Represented by Chemical Formula 1-2

[Chemical Formula 1-2]

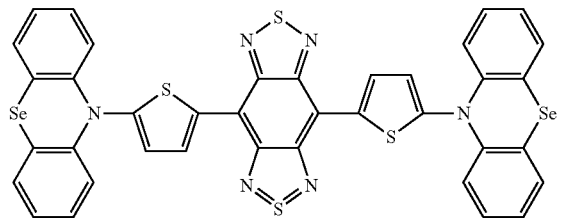

10-(5-(tributylstannyl)thiophen-2-yl)-10H-phenoselenazine (0.63 g, 1.02 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.24 g (Yield: 34%) of a product.

MALDI-TOF molecular weight analysis: 847 m/z

Synthesis Example 3: Synthesis of Compound Represented by Chemical Formula 1-3

[Chemical Formula 1-3]

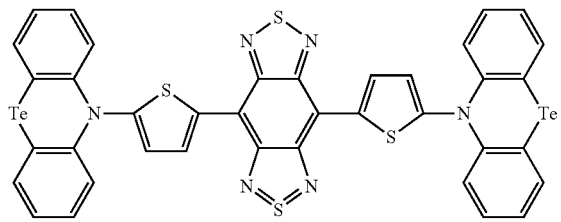

10-(5-(tributylstannyl)thiophen-2-yl)-10H-phenotellurazine (0.22 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated and evaporated, and dichloromethane is used for precipitation to obtain 0.08 g (Yield: 30%) of a product.

MALDI-TOF molecular weight analysis: 945 m/z

Synthesis Example 4: Synthesis of Compound Represented by Chemical Formula 1-4

[Chemical Formula 1-4]

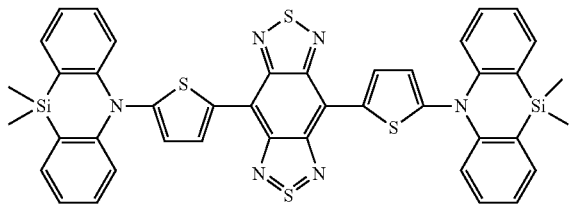

10,10-dimethyl-5-(5-(tributylstannyl)thiophen-2-yl)-5,10-dihydrodibenzo[b,e][1,4]azasiline (0.2 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated and evaporated, and dichloromethane is used for precipitation to obtain 0.08 g (Yield: 47%) of a product.

MALDI-TOF molecular weight analysis: 804 m/z

Synthesis Example 5: Synthesis of Compound Represented by Chemical Formula 1-5

[Chemical Formula 1-5]

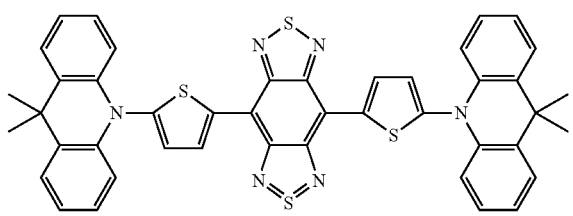

9,9-dimethyl-10-(5-(tributylstannyl)thiophen-2-yl)-9,10-dihydroacridine (0.99 g, 0.17 mmol), 4,8-dibromobenzo[1,2-c;4,5-c]bis([1,2,5]thiadiazole) (0.05 g, 0.14 mmol), and (tetrakis(triphenylphosphine)palladium (0) (0.004 g, 0.007 mmol) are dissolved in 5 ml of dry toluene and then, stirred at 110° C. for 18 hours. When a reaction is complete, the toluene is concentrated and evaporated, and dichloromethane is used for precipitation to obtain 0.023 g (Yield: 21%) of a product.

MALDI-TOF molecular weight analysis: 772 m/z

Synthesis Example 6: Synthesis of Compound Represented by Chemical Formula 1-6

[Chemical Formula 1-6]

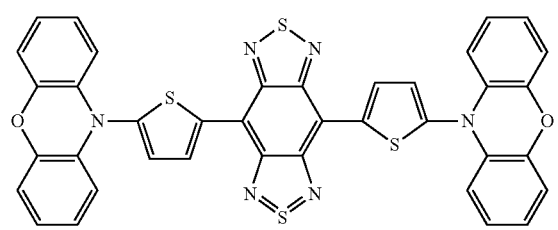

10-(5-(tributylstannyl)thiophen-2-yl)-10H-phenoxazine (0.57 g, 1.02 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.29 g (Yield: 47%) of a product.

MALDI-TOF molecular weight analysis: 720 m/z

Synthesis Example 7: Synthesis of Compound Represented by Chemical Formula 1-7

[Chemical Formula 1-7]

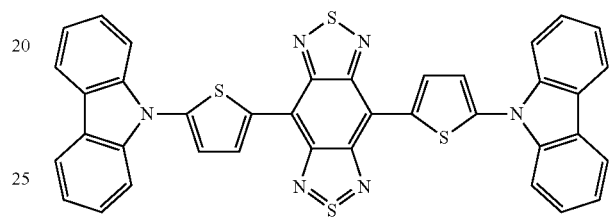

9-(5-(tributylstannyl)thiophen-2-yl)-9H-carbazole (1 g, 1.86 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 10 ml of dry toluene and then, stirred at 110° C. for 18 hours. When a reaction is complete, the toluene is concentrated and evaporated, and dichloromethane is used for precipitation to obtain 0.33 g (Yield: 56%) of a product.

MALDI-TOF molecular weight analysis: 688 m/z

Synthesis Example 8: Synthesis of Compound Represented by Chemical Formula 2-1

[Chemical Formula 2-1]

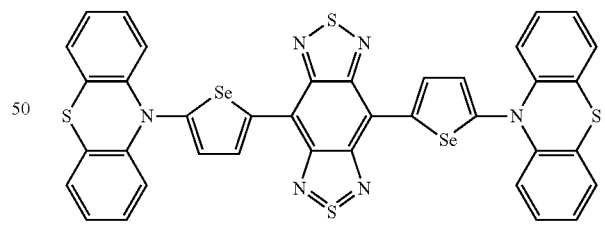

10-(5-(tributylstannyl)selenophen-2-yl)-10H-phenothiazine (0.63 g, 1.02 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.31 g (Yield: 43%) of a product.

MALDI-TOF molecular weight analysis: 847 m/z

Synthesis Example 9: Synthesis of Compound Represented by Chemical Formula 2-2

[Chemical Formula 2-2]

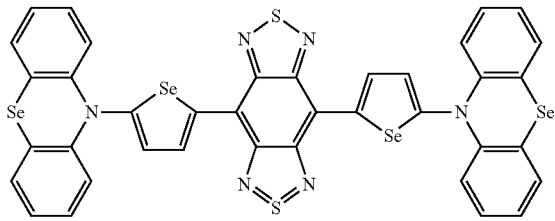

10-(5-(tributylstannyl)selenophen-2-yl)-10H-phenoselenazine (0.23 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated and evaporated, and dichloromethane is used for precipitation to obtain 0.09 g (Yield: 34%) of a product.

MALDI-TOF molecular weight analysis: 941 m/z

Synthesis Example 10: Synthesis of Compound Represented by Chemical Formula 2-3

[Chemical Formula 2-3]

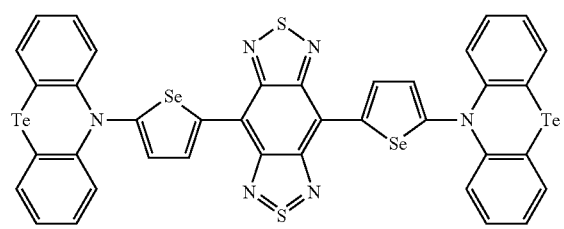

10-(5-(tributylstannyl)selenophen-2-yl)-10H-phenotellurazine (0.24 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated and evaporated, and dichloromethane is used for precipitation to obtain 0.05 g (Yield: 17%) of a product.

MALDI-TOF molecular weight analysis: 1041 m/z

Synthesis Example 11: Synthesis of Compound Represented by Chemical Formula 2-4

[Chemical Formula 2-4]

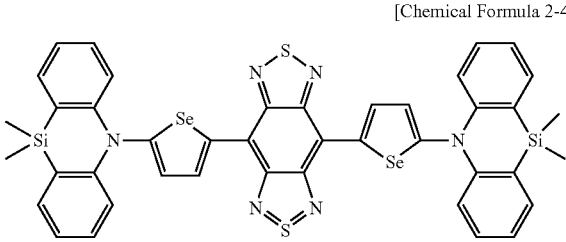

10,10-dimethyl-5-(5-(tributylstannyl)selenophen-2-yl)-5,10-dihydrodibenzo[b,e][1,4]azasiline (0.22 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated, and evaporated, and dichloromethane is used for precipitation to obtain 0.1 g (Yield: 32%) of a product.

MALDI-TOF molecular weight analysis: 900 m/z

Synthesis Example 12: Synthesis of Compound Represented by Chemical Formula 2-5

[Chemical Formula 2-5]

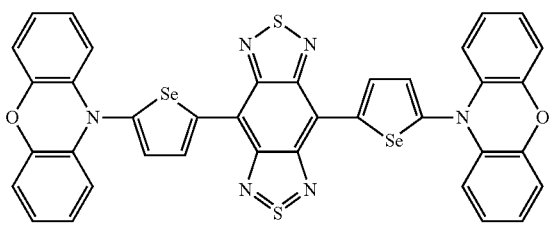

10-(5-(tributylstannyl)selenophen-2-yl)-10H-phenoxazine (0.61 g, 1.02 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.3 g (Yield: 43%) of a product.

MALDI-TOF molecular weight analysis: 815 m/z

Synthesis Example 13: Synthesis of Compound Represented by Chemical Formula 2-6

[Chemical Formula 2-6]

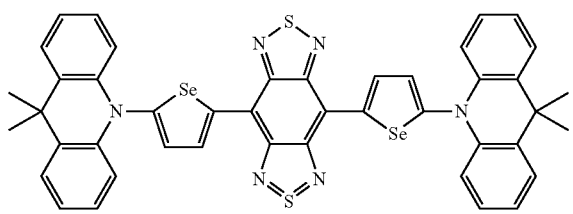

9,9-dimethyl-10-(5-(tributylstannyl)selenophen-2-yl)-9,10-dihydroacridine (0.11 g, 0.17 mmol), 4,8-dibromobenzo[1,2-c;4,5-c]bis([1,2,5]thiadiazole) (0.05 g, 0.14 mmol), tetrakis(triphenylphosphine)palladium (0) (0.004 g, 0.007 mmol) are dissolved in 5 ml of dry toluene and then, stirred at 110° C. for 18 hours. When a reaction is complete, the toluene is concentrated and evaporated, and dichloromethane is used for precipitation to obtain 0.02 g (Yield: 16%) of a product.

MALDI-TOF molecular weight analysis: 868 m/z

Synthesis Example 14: Synthesis of Compound Represented by Chemical Formula 2-7

[Chemical Formula 2-7]

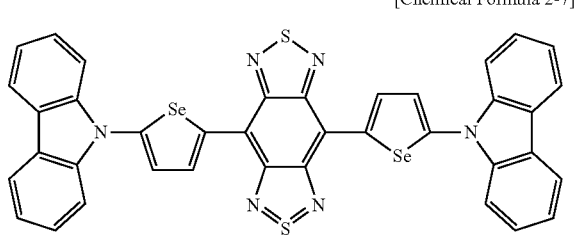

9-(5-(tributylstannyl)selenophen-2-yl)-9H-carbazole (0.55 g, 1.02 mmol), 4,8-dibromobenzo[1,2-c;4,5-c]bis([1,2,5]thiadiazole) (0.3 g, 0.85 mmol), and tetrakis(triphenylphosphine)palladium (0) (0.024 g, 0.043 mmol) are dissolved in 15 ml of dry toluene and then, stirred at 110° C. for 18 hours. When a reaction is complete, the toluene is concentrated and evaporated, and dichloromethane is used for precipitation to obtain 0.33 g (Yield: 50%) of a product.

MALDI-TOF molecular weight analysis: 783 m/z

Comparative Synthesis Example 1: Synthesis of Compound Represented by Chemical Formula 3-1

[Chemical Formula 3-1]

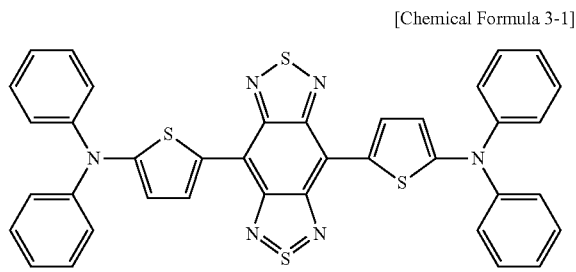 [SMILES: c1ccc(N(c2ccccc2)c2ccc(-c3c4c(c(-c5ccc(N(c6ccccc6)c6ccccc6)s5)c5nsnc35)N=S=N4)s2)cc1]

N,N-diphenyl-5-(tributylstannyl)thiophen-2-amine (0.18 g, 0.34 mmol), 4,8-dibromobenzo[1,2-c;4,5-c]bis([1,2,5]thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is concentrated and evaporated, and dichloromethane is used for precipitation to obtain 0.1 g (Yield: 52%) of a product.

MALDI-TOF molecular weight analysis: 692 m/z

Evaluation I

Maximum absorption wavelengths ($\lambda$max) of the compounds according to Synthesis Examples 1 to 14 are calculated in a ⌈Gaussian 09 program⌋ method by using B3LYP/6-31 G(d) level theory described in ⌈M. J. Frisch, et al., Gaussian 09, Revision D.01; Gaussian, Inc.: Wallingford, Conn. 2009⌋. The results of Synthesis Examples 1 to 5 and Synthesis Examples 8 to 13 are shown in Table 1.

TABLE 1

| | $\lambda_{max}$ (nm) |
|---|---|
| Synthesis Example 1 | 983 |
| Synthesis Example 2 | 986 |

TABLE 1-continued

| | $\lambda_{max}$ (nm) |
|---|---|
| Synthesis Example 3 | 998 |
| Synthesis Example 4 | 1004 |
| Synthesis Example 5 | 993 |
| Synthesis Example 8 | 1021 |
| Synthesis Example 9 | 1025 |
| Synthesis Example 10 | 1047 |
| Synthesis Example 11 | 1046 |
| Synthesis Example 12 | 1018 |
| Synthesis Example 13 | 1037 |

Referring to Table 1, the compounds according to Synthesis Examples 1 to 5 and 8 to 13 exhibit excellent wavelength absorption in a near-infrared wavelength region.

Evaluation II

Deposition characteristics of the compounds according to Synthesis Examples 1 to 14 and Comparative Synthesis Example 1 are evaluated. The deposition characteristics are evaluated by sublimating the compounds under high vacuum of less than or equal to 10 Pa and then, measuring a weight loss depending on a temperature increase in a thermogravimetric analysis method. The results of the compounds of Synthesis Examples 1 and 5 are shown in Table 2. The compound according to Comparative Synthesis Example 1 is decomposed during the deposition process and may not be evaluated.

TABLE 2

| | $T_s$(° C.) (−10 wt %) |
|---|---|
| Synthesis Example 1 | 330 |
| Synthesis Example 5 | 335 |

* $T_s$(° C.) (−10 wt %): temperatures where weights of the samples are decreased down by 10 wt %

Referring to Table 2, the compounds according to Synthesis Examples 1 and 5 exhibit excellent deposition characteristics.

Examples and Comparative Examples: Production of Photoelectric Device

A 150 nm-thick anode is formed by sputtering ITO on a glass substrate. Subsequently, each compound according to Synthesis Examples 1 to 14 on the anode is co-deposited with C60 in a 1:1 volume ratio, respectively, to form a 150 nm-thick active layer (photoelectric conversion layer). Then, C60 is deposited on the photoelectric conversion layer to form a 30 nm-thick auxiliary layer. Then, ITO is sputtered on the auxiliary layer to form a 7 nm-thick cathode. Aluminum oxide ($Al_2O_3$) is deposited on the cathode to form a 50 nm-thick anti-reflection layer and encapsulated with a glass plate to produce the photoelectric devices according to Examples 1 to 14.

On the other hand, the compound according to Comparative Synthesis Example 1 is decomposed during the deposition process, so that a thin film is not formed, so that a photoelectric device could not be produced.

Evaluation III

Figure 7:
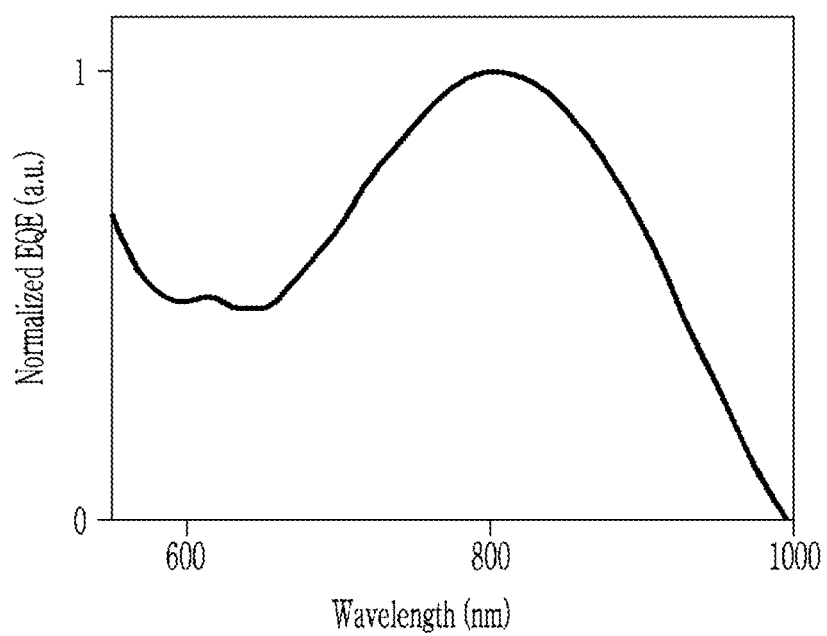
FIG. 7 is a graph showing external quantum efficiency of the photoelectric device according to Example 5.

Photoelectric conversion efficiency of the photoelectric devices according to Examples 1 to 14 is evaluated. The photoelectric conversion efficiency is measured by using an IPCE measurement system (TNE Technology Co., Ltd., Korea). First, the IPCE measurement system is calibrated by using an Si photodiode (Hamamatsu Photonics, K.K., Japan) and mounted on the photoelectric devices to measure external quantum efficiency within a wavelength range of about 400 nm to about 1000 nm. The result of the photoelectric device according to Example 5 is shown in FIG. 7. FIG. 7 is a graph showing external quantum efficiency of the photoelectric device according to Example 5. Referring FIG. 7, the photoelectric device according to Example 5 exhibits excellent external quantum efficiency in a near-infrared region (810 nm to about 910 nm).

While this disclosure has been described in connection with what is presently considered to be practical example embodiments, it is to be understood that the inventive concepts are not limited to the disclosed example embodiments. On the contrary, the inventive concepts are intended to cover various modifications and equivalent arrangements included within the spirit and scope of the appended claims.

DESCRIPTION OF SYMBOLS

10: first electrode
20: second electrode
30: active layer
50a, 50b, 50c: photo-sensing device
55: charge storage
70a, 70b, 70c: color filter
80: insulation layer
100, 200: photoelectric device
300, 400, 500: organic sensor

What is claimed is:

1. A near-infrared absorber, comprising:
a compound represented by Chemical Formula 1:

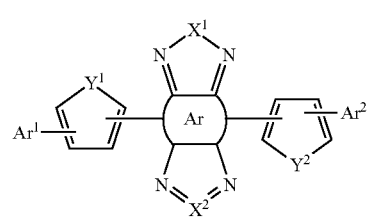

[Chemical Formula 1]

wherein, in Chemical Formula 1,
Ar is a substituted or unsubstituted C6 to C30 aromatic ring, a substituted or unsubstituted C3 to C30 heteroaromatic ring, or a combination thereof,
$X^1$ is O, S, Se, Te, S(=O), S(=O$_2$), NR$^a$, C(=O), CR$^b$R$^c$, or SiR$^d$R$^e$, wherein R$^a$, R$^b$, R$^c$, R$^d$, and R$^e$ are independently hydrogen, deuterium, C1 to C6 alkyl group, a C1 to C6 haloalkyl group, a halogen, or a cyano group,
$X^2$ is O, S, Se, Te, C, or S(=O),
$Y^1$ and $Y^2$ are independently O, S, Se, Te, S(=O), S(=O)$_2$, NR$^a$, SiR$^b$R$^c$, or CR$^d$R$^e$, wherein R$^a$, R$^b$, R$^c$, R$^d$, and R$^e$ are independently hydrogen, deuterium, C1 to C6 alkyl group, a C1 to C6 haloalkyl group, a halogen, or a cyano group, and
$Ar^1$ and $Ar^2$ are independently a functional group represented by Chemical Formula A,

[Chemical Formula A]

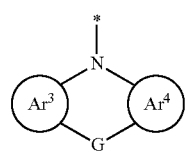

wherein, in Chemical Formula A,
$Ar^3$ and $Ar^4$ are independently a substituted or unsubstituted C6 to C30 arene group or a substituted or unsubstituted C3 to C30 heteroarene group, G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and

* is a linking point, wherein the near-infrared absorber has a peak absorption wavelength in a wavelength region of about 700 nm to about 3000 nm.

2. The near-infrared absorber of claim 1, wherein in Chemical Formula 1, Ar is an unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

3. The near-infrared absorber of claim 1, wherein in Chemical Formula 1, Ar is a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

4. The near-infrared absorber of claim 1, wherein Chemical Formula A is represented by one of Chemical Formula A-1 to Chemical Formula A-5:

[Chemical Formula A-1]

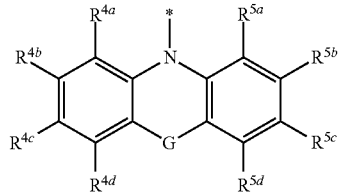

[Chemical Formula A-2]

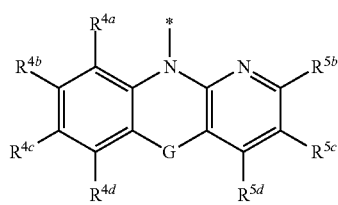

[Chemical Formula A-3]

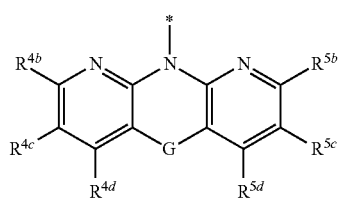

-continued

[Chemical Formula A-4]

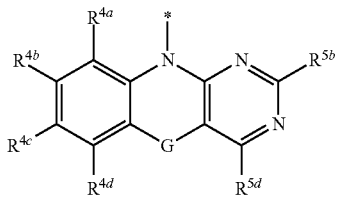

[Chemical Formula A-5]

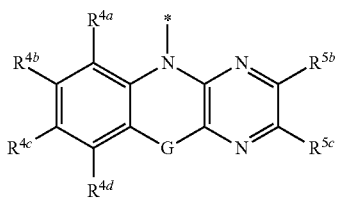

wherein, in Chemical Formula A-1,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5a}$ to R$^{5d}$ have structures such that
R$^{4a}$ to R$^{4d}$ and R$^{5a}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, and two adjacent groups of R$^{5a}$ to R$^{5d}$ are linked to each other to provide a 5-membered aromatic ring or a 6-membered aromatic ring, wherein, in Chemical Formula A-2,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5b}$ to R$^{5d}$ have structures such that
R$^{4a}$ to R$^{4d}$ and R$^{5b}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, and/or two adjacent groups of R$^{5b}$ to R$^{5d}$ are linked to each other to provide a 5-membered aromatic ring or a 6-membered aromatic ring, wherein, in Chemical Formula A-3,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4b}$ to R$^{4d}$ and R$^{5b}$ to R$^{5d}$ have structures such that
R$^{4b}$ to R$^{4d}$ and R$^{5b}$ and R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4b}$ to R$^{4d}$ are linked to each other to provide a 5-membered aromatic ring or a 6-membered aromatic ring, and two adjacent groups of R$^{5b}$ to R$^{5d}$ are linked to each other to provide a 5-membered aromatic ring or a 6-membered aromatic ring, wherein, in Chemical Formula A-4,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5b}$ and R$^{5d}$ have structures such that
R$^{4a}$ to R$^{4d}$ and R$^{5b}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of R$^{4a}$ to R$^{4d}$ are linked to each other to provide a 5-membered aromatic ring or a 6-membered aromatic ring, wherein, in Chemical Formula A-5,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))— wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and $R^{4a}$ to $R^{4d}$ and $R^{5b}$ and $R^{5c}$ have structures such that
  $R^{4a}$ to $R^{4d}$ and $R^{5b}$ to $R^{5c}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
  two adjacent groups of $R^{4a}$ to $R^{4d}$ are linked to each other to provide a 5-membered aromatic ring or a 6-membered aromatic ring, and/or two adjacent groups of $R^{5b}$ and $R^{5c}$ are linked to each other to provide a 5-membered aromatic ring or a 6-membered aromatic ring.

5. A near-infrared absorbing/blocking film comprising the near-infrared absorber of claim 1.

6. A photoelectric device, comprising:
  a first electrode and a second electrode facing each other; and
  an active layer disposed between the first electrode and the second electrode,
  wherein the active layer includes a near-infrared absorber that includes a compound represented by Chemical Formula 1:

[Chemical Formula 1]

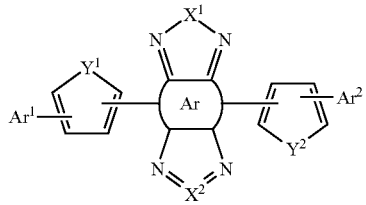

wherein, in Chemical Formula 1,
  Ar is a substituted or unsubstituted C6 to C30 aromatic ring, a substituted or unsubstituted C3 to C30 heteroaromatic ring, or a combination thereof,
  $X^1$ is O, S, Se, Te, S(=O), S(=O$_2$), NR$^a$, C(=O), CR$^b$R$^c$, or SiR$^d$R$^e$ wherein R$^a$, R$^b$, R$^c$, R$^d$, and R$^e$ are independently hydrogen, deuterium, C1 to C6 alkyl group, a C1 to C6 haloalkyl group, a halogen, or a cyano group,
  $X^2$ is O, S, Se, Te, C, or S(=O),
  $Y^1$ and $Y^2$ are independently O, S, Se, Te, S(=O), S(=O)$_2$, NR$^a$, SiR$^b$R$^c$, or CR$^d$R$^e$, wherein R$^a$, R$^b$, R$^c$, R$^d$, and R$^e$ are independently hydrogen, deuterium, a C1 to C6 alkyl group, a C1 to C6 haloalkyl group, a halogen, or a cyano group, and
  Ar$^1$ and Ar$^2$ are independently a functional group represented by Chemical Formula A,

[Chemical Formula A]

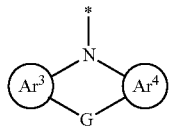

wherein, in Chemical Formula A,
  Ar$^3$ and Ar$^4$ are independently a substituted or unsubstituted C6 to C30 arene group or a substituted or unsubstituted C3 to C30 heteroarene group, G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and

* is a linking point,
wherein the near-infrared absorber has a peak absorption wavelength in a wavelength region of about 700 nm to about 3000 nm.

7. The photoelectric device of claim 6, wherein Ar is an unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

8. The photoelectric device of claim 6, wherein Ar is a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

9. The photoelectric device of claim 6, wherein Chemical Formula A is represented by one of Chemical Formula A-1 to Chemical Formula A-5:

[Chemical Formula A-1]

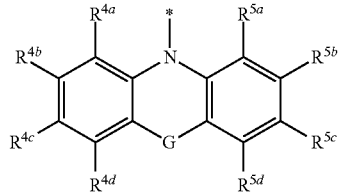

[Chemical Formula A-2]

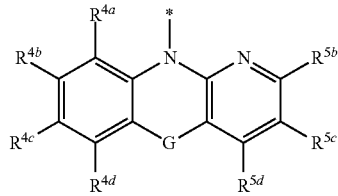

[Chemical Formula A-3]

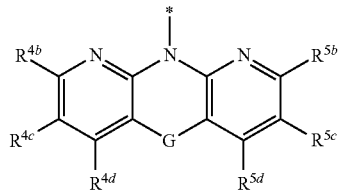

[Chemical Formula A-4]

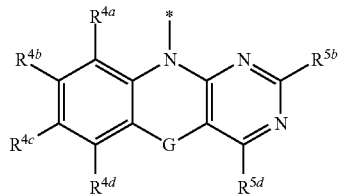

-continued

[Chemical Formula A-5]

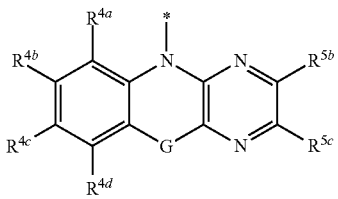

wherein, in Chemical Formula A-1,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5a}$ to R$^{5d}$ have structures such that
R$^{4a}$ to R$^{4d}$ and R$^{5a}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, and/or two adjacent groups of R$^{5a}$ to R$^{5d}$ are linked to each other to provide a 5-membered aromatic ring or a 6-membered aromatic ring, wherein, in Chemical Formula A-2,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5b}$ to R$^{5d}$ have structures such that
R$^{4a}$ to R$^{4d}$ and R$^{5b}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, and/or two adjacent groups of R$^{5b}$ to R$^{5d}$ are linked to each other to provide a 5-membered aromatic ring or a 6-membered aromatic ring, wherein, in Chemical Formula A-3,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4b}$ to R$^{4d}$ and R$^{5b}$ to R$^{5d}$ have structures such that
R$^{4b}$ to R$^{4d}$ and R$^{5b}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4b}$ to R$^{4d}$ are linked to each other to provide a 5-membered aromatic ring or a 6-membered aromatic ring, and/or two adjacent groups of R$^{5b}$ to R$^{5d}$ are linked to each other to provide a 5-membered aromatic ring or a 6-membered aromatic ring, wherein, in Chemical Formula A-4,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5b}$ and R$^{5d}$ have structures such that
R$^{4a}$ to R$^{4d}$ and R$^{5b}$ to R$^{5d}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, wherein, in Chemical Formula A-5,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or linked to each other to form a ring, and n of —(CR$^f$R$^g$)$_n$— is an integer of 1 or 2, and R$^{4a}$ to R$^{4d}$ and R$^{5b}$ and R$^{5c}$ have structures such that
R$^{4a}$ to R$^{4d}$ and R$^{5b}$ to R$^{5c}$ are independently hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or
two adjacent groups of R$^{4a}$ to R$^{4d}$ are linked to each other to provide a 5-membered aromatic ring or a 6-membered aromatic ring, and/or two adjacent groups of $R^{5b}$ and $R^{5c}$ are linked to each other to provide a 5-membered aromatic ring or a 6-membered aromatic ring.

10. The photoelectric device of claim 6, wherein the active layer further comprises fullerene or a fullerene derivative.

11. An organic sensor comprising the photoelectric device of claim 6.

12. An electronic device comprising the organic sensor of claim 11.

13. An electronic device comprising the photoelectric device of claim 6.

14. The near-infrared absorber of claim 1, wherein $X^2$ is S, Se, or Te.

15. The photoelectric device of claim 6, wherein $X^2$ is S, Se, or Te.

* * * * *